US008460350B2

(12) United States Patent
Albertorio et al.

(10) Patent No.: US 8,460,350 B2
(45) Date of Patent: Jun. 11, 2013

(54) GRAFT PROTECTION MESH AND FIXATION TECHNIQUE

(75) Inventors: Ricardo Albertorio, Naples, FL (US); David C. Koogle, Jr., Bonita Springs, FL (US); Jacob A. Jolly, Naples, FL (US)

(73) Assignee: Arthrex, Inc., Naples, FL (US)

( * ) Notice: Subject to any disclaimer, the term of this patent is extended or adjusted under 35 U.S.C. 154(b) by 380 days.

(21) Appl. No.: 12/815,200

(22) Filed: Jun. 14, 2010

(65) Prior Publication Data

US 2010/0324608 A1 Dec. 23, 2010

Related U.S. Application Data

(60) Provisional application No. 61/218,773, filed on Jun. 19, 2009.

(51) Int. Cl.
*A61B 17/68* (2006.01)
(52) U.S. Cl.
USPC ........................................... 606/322
(58) Field of Classification Search
USPC ....... 606/213–221, 300–331; 623/13.11–13.2
See application file for complete search history.

(56) References Cited

U.S. PATENT DOCUMENTS

| 4,467,478 | A | * | 8/1984 | Jurgutis | 623/13.17 |
|---|---|---|---|---|---|
| 4,605,414 | A | * | 8/1986 | Czajka | 128/898 |
| 5,456,721 | A | * | 10/1995 | Legrand | 623/13.15 |
| 6,432,121 | B1 | | 8/2002 | Jervis | |
| 6,602,290 | B2 | * | 8/2003 | Esnouf et al. | 623/13.16 |
| 6,746,483 | B1 | * | 6/2004 | Bojarski et al. | 623/13.14 |
| 7,407,512 | B2 | * | 8/2008 | Bojarski et al. | 623/13.14 |
| 8,226,716 | B2 | * | 7/2012 | Mckernan et al. | 623/13.17 |
| 8,273,106 | B2 | * | 9/2012 | Stone et al. | 606/232 |
| 2002/0116070 | A1 | | 8/2002 | Amara et al. | |
| 2004/0024456 | A1 | * | 2/2004 | Brown et al. | 623/13.15 |
| 2005/0038426 | A1 | * | 2/2005 | Chan | 606/60 |
| 2007/0213819 | A1 | * | 9/2007 | McKernan et al. | 623/13.11 |
| 2008/0119929 | A1 | | 5/2008 | Schmieding et al. | |

FOREIGN PATENT DOCUMENTS

FR 2 769 825 A1 4/1999

\* cited by examiner

*Primary Examiner* — Kevin Truong
*Assistant Examiner* — Christopher Beccia
(74) *Attorney, Agent, or Firm* — Dickstein Shapiro LLP

(57) ABSTRACT

A three-dimensional mesh or screen in the shape of a simple flat piece of material that can be provided adjacent the graft (i.e., in between graft bundles, or around the graft, or between the graft and the fixation device) for improved strength and structural support for graft fixation. The mesh provides improved methods for installing and securing ligament grafts (such as double-bundle cruciate ligament grafts) with enhanced reconstruction results.

5 Claims, 17 Drawing Sheets

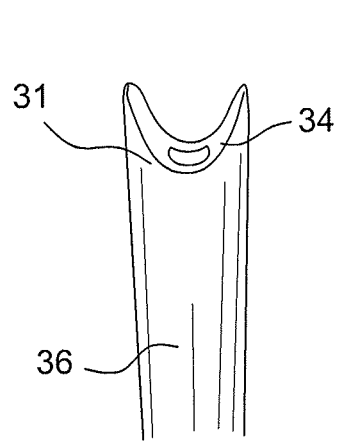
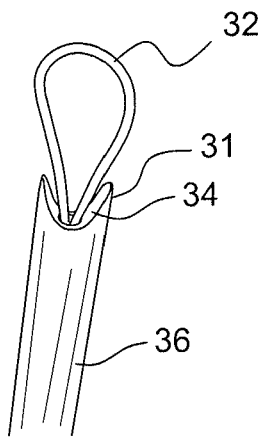
FIG. 7   FIG. 8
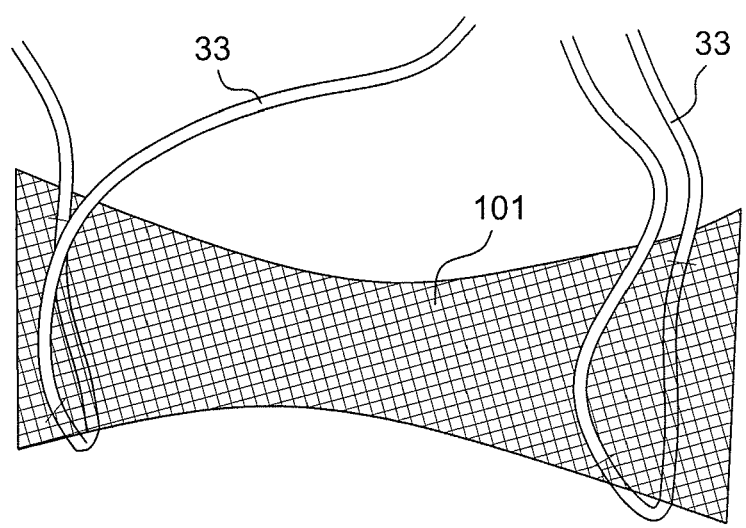
FIG. 9

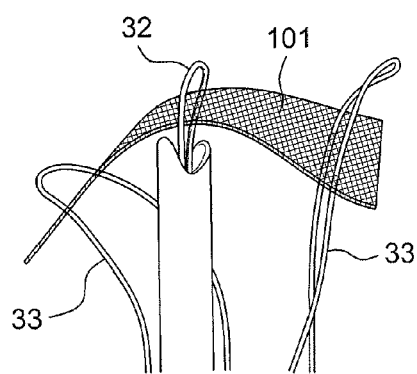
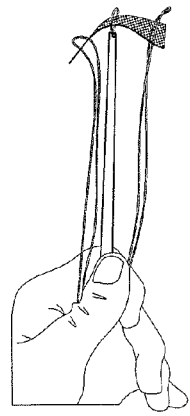
FIG. 10  FIG. 11
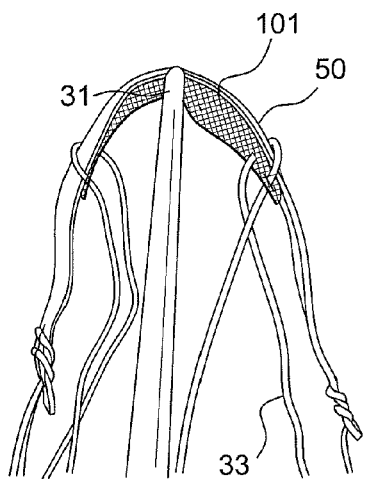
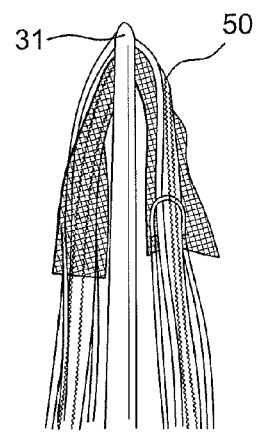
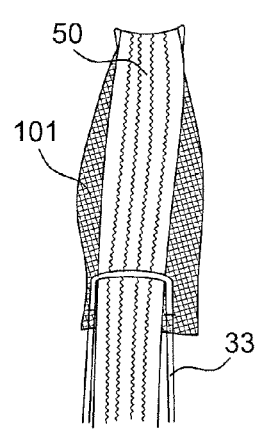
FIG. 12  FIG. 13  FIG. 14

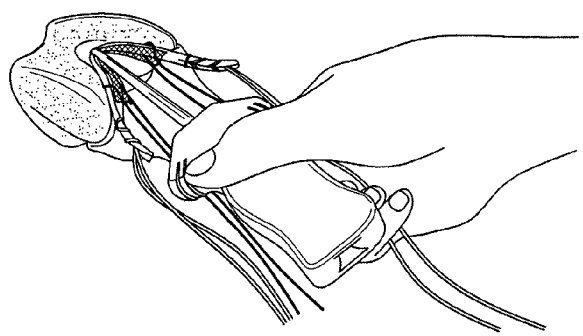 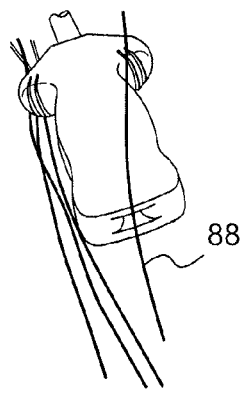
FIG. 17(a)　　FIG. 17(b)
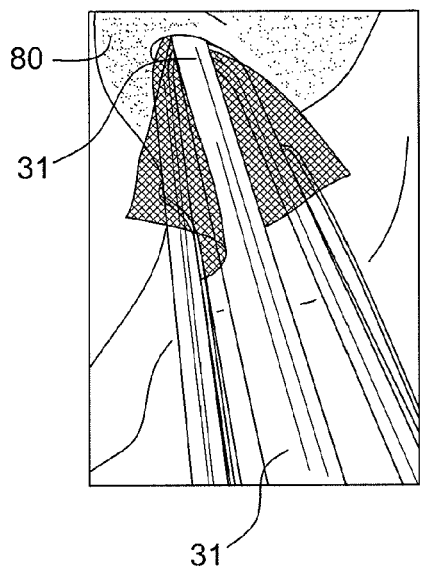 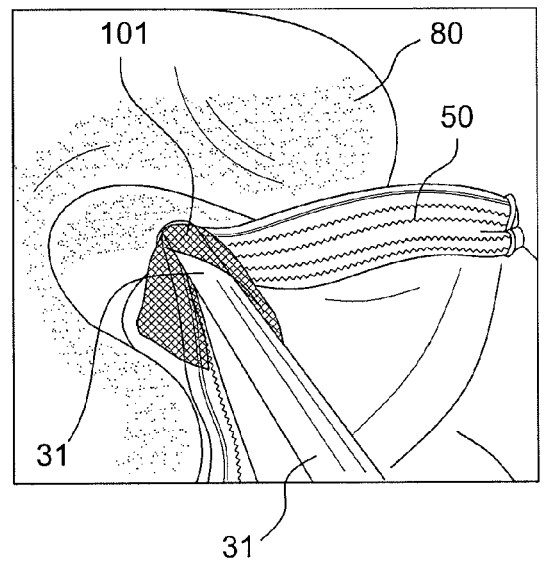
FIG. 18(a)　　FIG. 18(b)

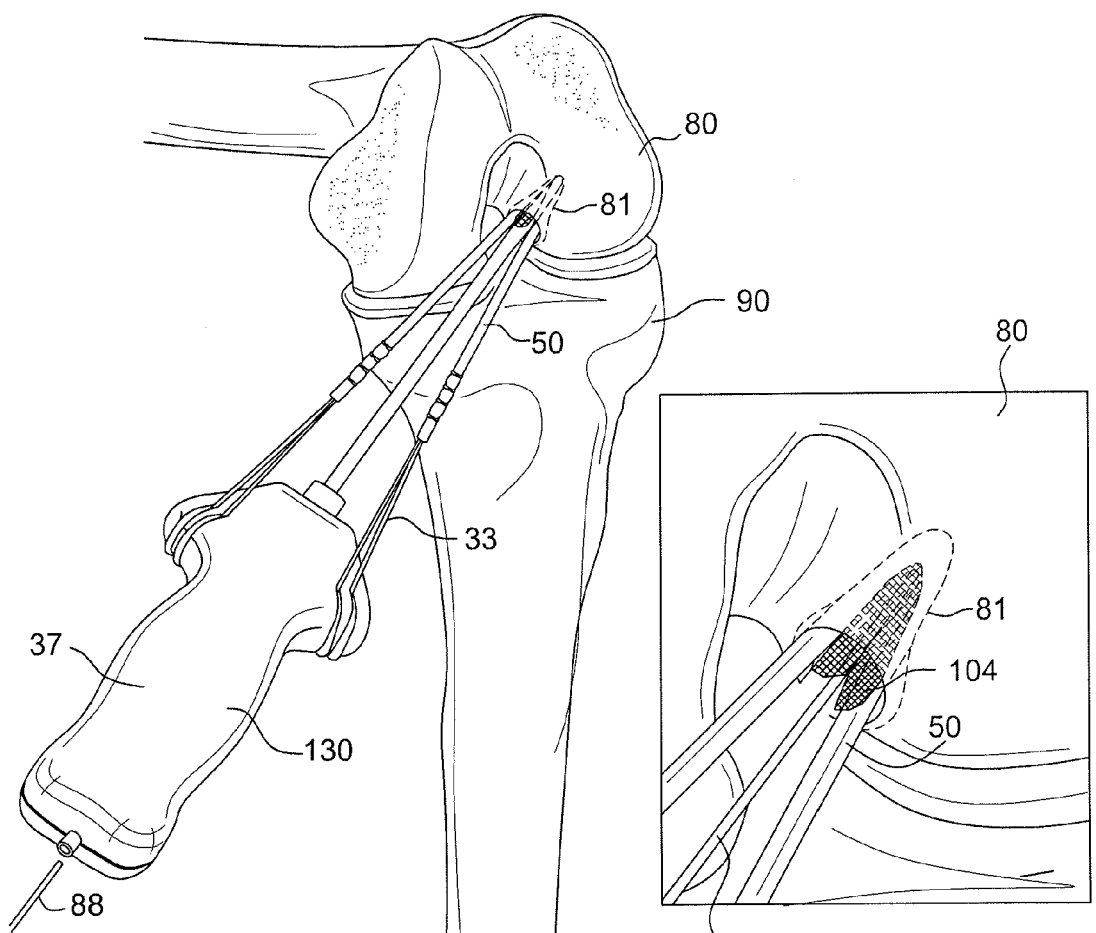
FIG. 38
FIG. 39
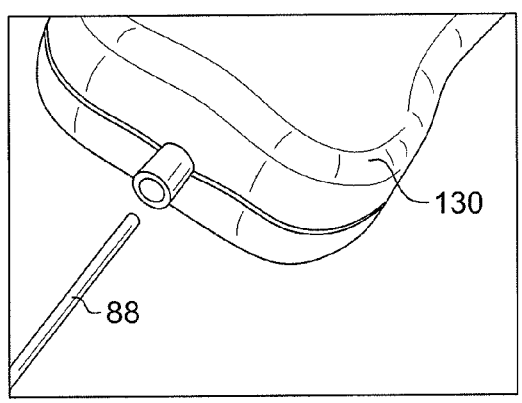
FIG. 40

GRAFT PROTECTION MESH AND FIXATION TECHNIQUE

CROSS REFERENCE TO RELATED APPLICATIONS

This application claims the benefit of U.S. Provisional Application Ser. No. 61/218,773, filed Jun. 19, 2009, the entire disclosure of which is incorporated by reference herein.

BACKGROUND OF THE INVENTION

1. Field of the Invention

The present invention is directed to fixation of tissue to bone and, more specifically, to a mesh for protecting tissue that is fixated within bone tunnels.

2. Description of the Related Art

When soft tissue tears away from bone, reattachment becomes necessary. Cruciate ligament reconstruction is routinely performed by creating femoral and tibial tunnels into which ligament grafts are secured. Various graft types are used to replace the native cruciate ligament. For example, anatomic double-bundle cruciate ligament reconstruction has been shown by biomechanical studies to be superior in restoring normal knee laxity compared with conventional single-bundle isometric reconstructions.

Fixation of a ligament graft (such as a double-bundle cruciate ligament) typically requires positioning of the ligament graft within the bone tunnel or socket, and then inserting a fixation device (such as a bone screw, for example) between the graft and the internal wall of the bone tunnel or socket. A double-bundle ligament fixation technique is detailed, for example, in U.S. Patent Publ. No. 2008/0119929, filed on Jan. 28, 2008, the disclosure of which is incorporated by reference herein. In securing the graft within the bone tunnel/socket using a fixation device, it is important that the graft be rigidly fixed within the tunnel or socket to prevent slippage or displacement of the graft, as well as rotation of the graft within the tunnel or socket. It is also important to ensure that the fixation device does not damage the graft during insertion (i.e., to minimize graft laceration).

SUMMARY OF THE INVENTION

The present invention provides a three-dimensional mesh or screen in the shape of a simple flat piece of material that can be provided adjacent the graft (i.e., between the graft and the fixation device, or in between graft bundles, or around the graft) for improved strength and structural support for graft fixation. The mesh of the present invention provides improved methods for installing and securing ligament grafts (such as double-bundle cruciate ligament grafts) with enhanced reconstruction results.

The three-dimensional mesh may be formed of a bioabsorbable or non-absorbable material and may comprise fibers which are weaved, laced, crosslinked, or glued together, for example. In an exemplary embodiment, the three-dimensional mesh may be provided by molding a suitable pre-polymeric compound into a shape which directly provides the desired mesh structure. In an alternative embodiment, the three-dimensional mesh may be provided as a "one size fits all" flat piece or sheet that may be sized to a desired shape (for example, to a "bow-tie" or "flower" configuration) by medical personnel.

The three-dimensional mesh provides enhanced fixation of soft tissue (such as ligament grafts) to bone. The mesh reduces the insertion torque of the fixation device, eliminates the need for whipstitching, and reduces displacement of the graft within the tunnel during fixation. The three-dimensional mesh also decreases the graft slippage, increasing therefore the maximum load to failure. Because of its collapsible design, the mesh of the present invention allows easier insertion of the graft within tunnels or sockets. The "one size fits all" mesh is used in various bone tunnels and/or with various screw diameters. The perforations in the mesh also allow for healing through the mesh and/or delivery of substances that promote healing such as ACP or PRP. Moreover, it will not inhibit resorption or degradation of absorbable fixation methods such as polymeric screws.

BRIEF DESCRIPTION OF THE DRAWINGS

Other features and advantages of the present invention will become apparent when the following detailed description is read in conjunction with the accompanying drawings, in which:

FIGS. 5-11 illustrate a driver/mesh assembly with a driver configured for inserting a graft mesh according to an embodiment of the present invention;

FIGS. 12-20 illustrate subsequent steps of a femoral fixation technique employing the driver/mesh assembly of FIG. 11, and according to an embodiment of the present invention;

FIGS. 36-42 illustrate subsequent steps of a femoral fixation technique employing the driver/mesh assembly of FIG. 31, and according to an embodiment of the present invention.

DETAILED DESCRIPTION OF THE PREFERRED EMBODIMENT

Figure 1:
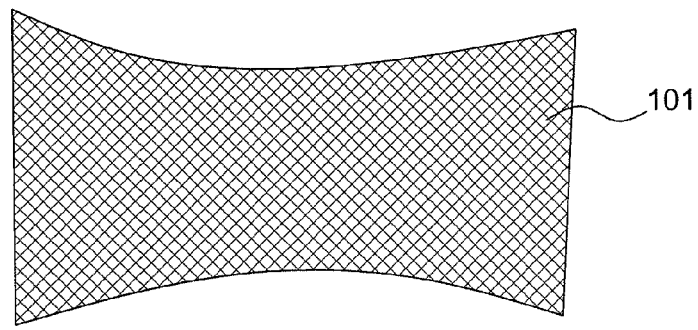
FIG. 1 illustrates a mesh according to a first exemplary embodiment of the present invention.

The following description is provided to enable any person skilled in the art to make and use the invention and sets forth the best modes contemplated by the inventors of carrying out their invention. Various modifications, however, will remain readily apparent to those skilled in the art.

The present invention provides a three-dimensional mesh or screen in the shape of a simple flat piece of material that can be provided adjacent the graft (i.e., between the graft and the fixation device, or in between graft bundles, or around the graft) for improved strength and structural support for graft fixation. The mesh of the present invention protects the soft tissue graft from laceration and/or rotation or displacement of the graft when fixing the graft within a bone tunnel (or socket) with a fixation device (for example, a screw). The mesh also prevents shearing of the threads of the fixation device (screw) against the graft. The collapsible design of the mesh of the present invention allows it to be inserted into tight spaces and/or to be used with fixation devices (for example, screws) of various diameters.

The three-dimensional mesh of the present invention may be formed of a bioabsorbable or non-absorbable material and may comprise fibers which are woven, laced, crosslinked, or glued together, for example. In an exemplary embodiment, the three-dimensional mesh may be provided by molding a suitable pre-polymeric compound into a shape which directly provides the desired mesh structure. In an alternative embodiment, the three-dimensional mesh may be provided as a "one size fits all" flat piece or sheet that may be sized to a desired shape (for example, to a "bow-tie" or "flower" configuration) by medical personnel (during the surgical procedure, for example). In yet additional embodiments, the three-dimensional mesh may be provided with at least one flexible region or section and at least one inflexible region or section. For example, the mesh may be provided with a flexible, middle region of the bow-tie and with adjacent inflexible, end regions of the bow-tie.

The three-dimensional mesh may be also provided with therapeutic agents and/or biological products such as bone marrow aspirate (BMA) and autologous bodily fluids (for example, blood, platelet rich plasma (PRP), autologous conditioned plasma (ACP) or growth factors), for delivering of such therapeutic agents and/or biological products to different surgical sites (for example, the distal femur during ACL surgery) during arthroscopic surgery. The therapeutic agents and/or biological products may be contained within a containment system comprising a carrier (such as collagen carrier, for example) and the network of relief structures (i.e., perforations, slits and/or holes formed within the mesh). The therapeutic agents and/or biological products may be provided on or within the mesh by various methods known in the art, such as immersion of the mesh within a solution of such agents and/or biological products, spraying or coating of the mesh with a solution of such agents and/or biological products, or directly incorporating the therapeutic agents and/or biological products into the material of the mesh (by blending the therapeutic agents and/or biological products with at least one material forming the mesh matrix during the mesh fabrication), among others.

According to exemplary embodiments only, the therapeutic agents and/or biological products may include bone marrow stromal cells (BMSCs) or mesenchymal cells isolated from bone marrow aspirate, having osteogenic and/or osteoinductive cell proliferative activity. The BMSCs or the mesenchymal cells may be isolated at the time of surgery (intraoperatively) and they may be collected from various sites such as iliac crest, proximal humeral head or distal femur. The BMSCs or the mesenchymal cells may be employed or combined with the mesh to facilitate slow release of the cells at the treatment site (i.e., within the bone tunnel or socket) and/or provide a structure for developing tissue (bone). The therapeutic agents and/or biological products are contained or encapsulated within the mesh and delivered at the surgical site.

Additional components such as autologous conditioned plasma (ACP), platelet-rich plasma (PRP), growth factors, additional antiseptic chemicals and/or antibiotics and/or electrolytes, or hormones or site-specific hybrid proteins (that promote or enhance the wound healing effectiveness of the growth factors) may be additionally or alternatively provided as part of the fixation system of the present invention (i.e., embedded, impregnated, or blended within the mesh).

The three-dimensional mesh provides enhanced fixation of soft tissue (such as ligament grafts) to bone, by reducing the insertion torque of the fixation device and, thus, eliminating whipstitching and/or displacement of the graft within the tunnel. The three-dimensional mesh also decreases the graft slippage, increasing therefore the maximum load to failure. Because of its collapsible design, the mesh of the present invention allows easier insertion of the graft within tunnels or sockets. The "one size fits all" mesh is used in various bone tunnels or sockets and/or with various screw diameters.

FIGS. 1-4 and 30 illustrate a three-dimensional mesh 101, 102, 103, 104 according to exemplary embodiments of the present invention. FIGS. 5-11 illustrate a driver/mesh assembly of the present invention with driver 30 designed to be employed with the mesh 101, 102, 103, 104. FIGS. 12-20 illustrate exemplary steps of a femoral fixation technique employing the driver/mesh assembly of FIG. 11, while FIGS. 21-29 illustrate exemplary steps of a tibial fixation technique employing the driver/mesh assembly of FIG. 11. FIGS. 31-35 illustrate a driver/mesh assembly of the present invention with driver 130 designed to be employed with the mesh 104. FIGS. 36-42 illustrate exemplary steps of a femoral fixation technique employing the driver/mesh assembly of FIG. 31.

According to an embodiment of the invention, and as shown in FIG. 1, mesh 101 is provided in a "bow-tie" configuration that allows the mesh to be easily inserted into a bone tunnel or socket (by employing a driver, for example) or, alternatively, to be wrapped around a portion of the graft, or around an interference fixation (such as a screw) for positioning of the screw within the tunnel and/or between the graft and the tunnel. The narrow middle width of the mesh 101 allows the mesh to be easily inserted into narrow bone tunnels or sockets, without being bunched up during insertion within the tunnel or socket. In addition, as the mesh is provided as a flat, simple sheet (and not having a tubular configuration), the mesh may be easily fitted around the graft or fixation device (as it is more difficult to fit a tube around a graft or fixation device).

Figure 2:
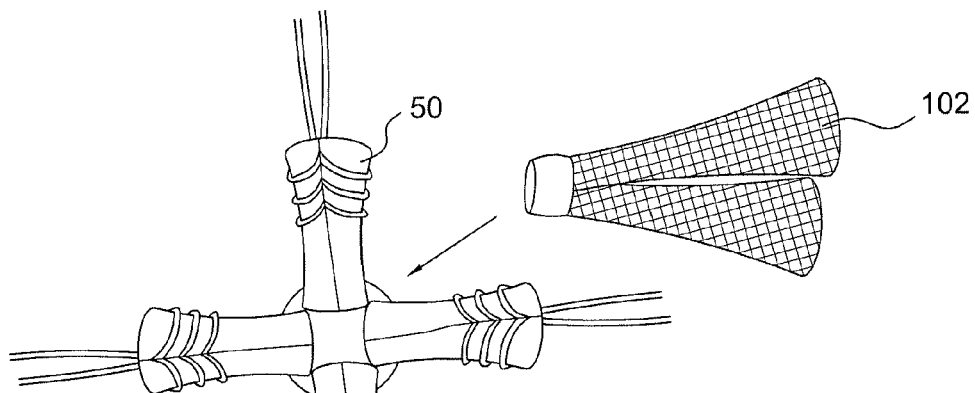
FIG. 2 illustrates a mesh according to a second exemplary embodiment of the present invention.
Figure 3:
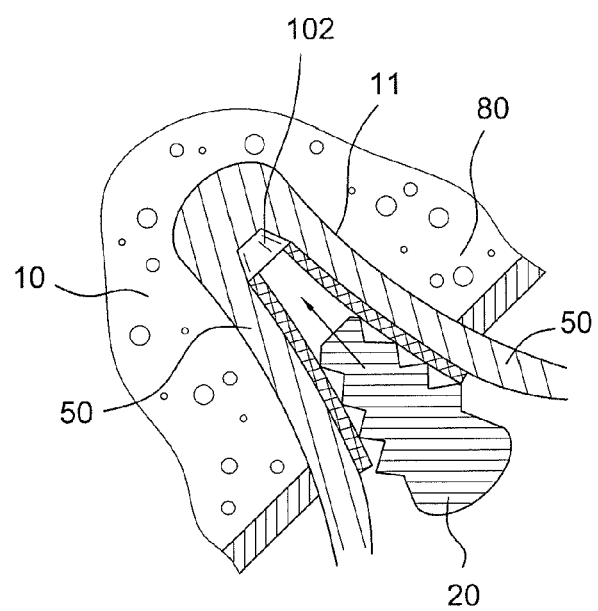
FIG. 3 is another view of the mesh of FIG. 2 (inserted in between the graft and fixation device)

FIGS. 2 and 3 illustrate mesh 102 of the present invention having an exemplary conical shape, such as a badminton shuttlecock with individual wings (segments), for example. FIG. 2 shows mesh 102 in the vicinity of a four-stranded graft 50. FIG. 3 shows mesh 102 fixating at least one strand of the four-stranded graft 50 against fixation device (screw) 20 secured within bone tunnel 11 of bone 10.

Figure 4:
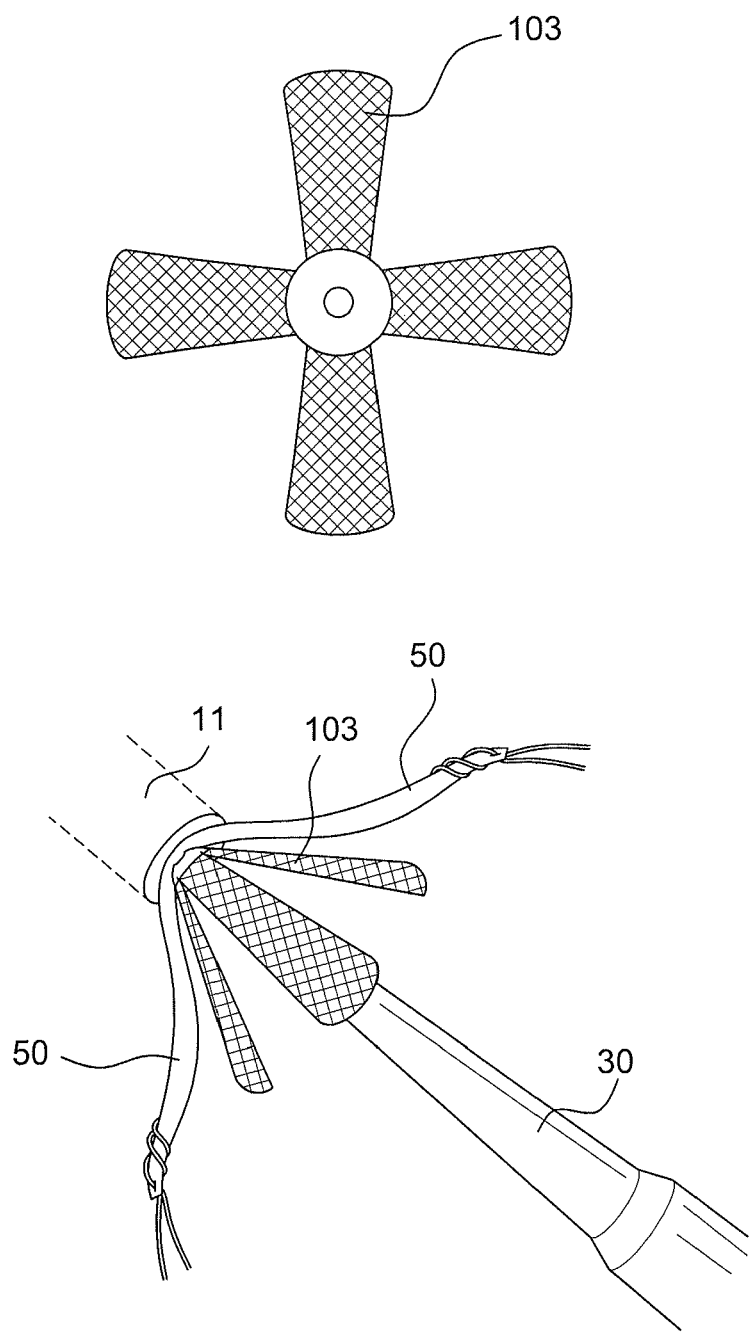
FIG. 4 illustrates a mesh according to a third exemplary embodiment of the present invention.

FIG. 4 illustrates mesh 103 of the present invention having an exemplary flat, flower-like configuration (i.e., with an exemplary four "petals" configuration) and being inserted by driver 30 within bone tunnel 11. According to a method of the present invention, the mesh 103 may be first wrapped around at least a portion of the graft or the graft folded over the mesh, and then the graft (together with the mesh) introduced within the tunnel or socket, followed by the insertion of the fixation device. Alternatively, the graft may be first introduced within the tunnel or socket, and then the fixation device (with the mesh wrapped around at least a portion of the fixation device) may be inserted within the bone tunnel to fixate the graft. In yet additional embodiments, the mesh 103 may be first introduced within tunnel 11 and then the graft with the fixation device (interference screw) introduced thereafter.

Figure 30:
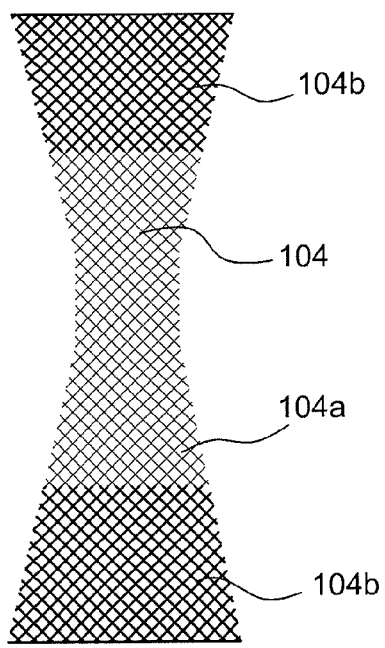
FIG. 30 illustrates a mesh according to a fourth exemplary embodiment of the present invention.
Figure 31:
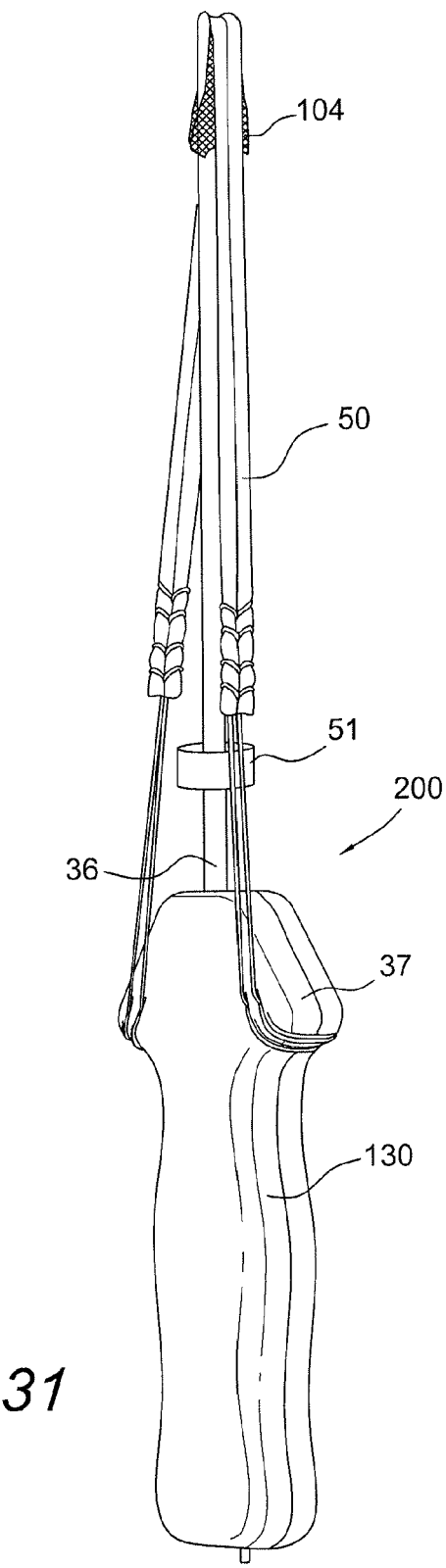
FIGS. 31-35 illustrate various views of a driver/mesh assembly with a driver configured for inserting the graft mesh of FIG. 30, and according to an embodiment of the present invention.
Figure 32:
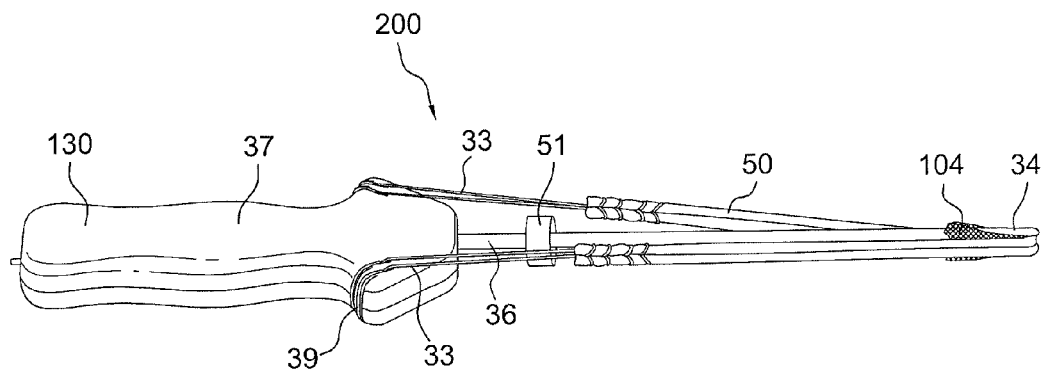

FIG. 30 illustrates mesh 104 of the present invention, which is similar in part to the mesh 101 of FIG. 1 (in that mesh 104 also has a "bow-tie" configuration) but differs from mesh 101 in that mesh 104 is provided with a middle region 104a and two ends regions 104b. In exemplary embodiments, the middle region 104a may have a different composition (texture) from the end regions 104b (for example, the middle region 104a may be reinforced so that it does not tear upon insertion). In additional embodiments, the middle region 104a may have a color contrasting from the color(s) of the end regions 104b.

The "bow-tie" configuration of mesh 104 allows the mesh to be easily inserted into a bone tunnel or socket (by employing a driver, for example) or, alternatively, to be wrapped around a portion of the graft, or around an interference fixation (such as a screw) for positioning of the screw within the tunnel and/or between the graft and the tunnel. The narrow middle width of region 104a of the mesh 104 allows the mesh to be easily inserted into narrow bone tunnels or sockets, without being bunched up during insertion within the tunnel or socket. In addition, as the mesh is provided as a flat, simple sheet (and not having a tubular configuration), the mesh 104 may be easily fitted around the graft or fixation device (as it is more difficult to fit a tube around a graft or fixation device). Preferably, the graft is folded over (looped over) the mesh 104 or the mesh 104 is wrapped around at least a portion of the graft, and then the graft (together with the mesh) introduced within the tunnel or socket, followed by the insertion of the fixation device. In yet additional embodiments, the graft may be first introduced within the tunnel or socket, and then the fixation device (with the mesh wrapped around at least a portion of the fixation device) may be inserted within the bone tunnel to fixate the graft. In yet additional embodiments, mesh 104 may be first introduced within tunnel 81 and then the graft with the fixation device (interference screw) introduced thereafter.

Mesh 101, 102, 103, 104 is preferably three-dimensional and comprises fibers which are woven, laced, crosslinked, or glued together, for example. In an alternative embodiment, the three-dimensional mesh may be provided by molding a suitable pre-polymeric compound into a shape which directly provides the desired mesh structure. The three-dimensional mesh may be formed of a bioabsorbable or non-absorbable material. A known bioabsorbable material is non-crystalline, amorphous poly (L-lactide-co-D,L-lactide) 70%:30% (PLDLA) copolymer, as this material reduces tissue reaction and generally degrades within 12 to 16 months. Although PLDLA may be a preferred material, other bioabsorbable materials known in the art can be utilized. As used in this application, bioabsorbable is considered to be interchangeable with biodegradable, resorbable and absorbable to mean that the mesh (or at least a portion of the mesh) can be absorbed by the body over time.

The three-dimensional mesh 101, 102, 103, 104 may be also formed of various synthetic materials such as Ultra High Molecular Weight Polyethylene, PEEK, metals or metal alloys (for example, provided as thin wires). In an alternative embodiment, mesh 101, 102, 103, 104 may comprise collagen fibers that provide a growth matrix for tissue once the bioabsorbable material of the mesh degrades. As detailed above, the mesh of the present invention may be also provided with regions or sections formed of same or different materials and/or may be formed of regions or sections having different colors to allow easy identification of different parts of the mesh during surgical fixation of graft and mesh (such as mesh 104 of FIG. 30).

The openings (or perforations or slits) in the mesh 101, 102, 103, 104 provide access for ingrowth of bony tissue for enhanced pullout strength. The openings also provide bioabsorbable materials from the mesh (the screen) and/or blood to pass through the slots and enhance tissue healing, and allow for uninhibited hydrolytic breakdown of typical bioabsorbable materials used to manufacture fixation devices (e.g., PLLA screws).

Figure 5:
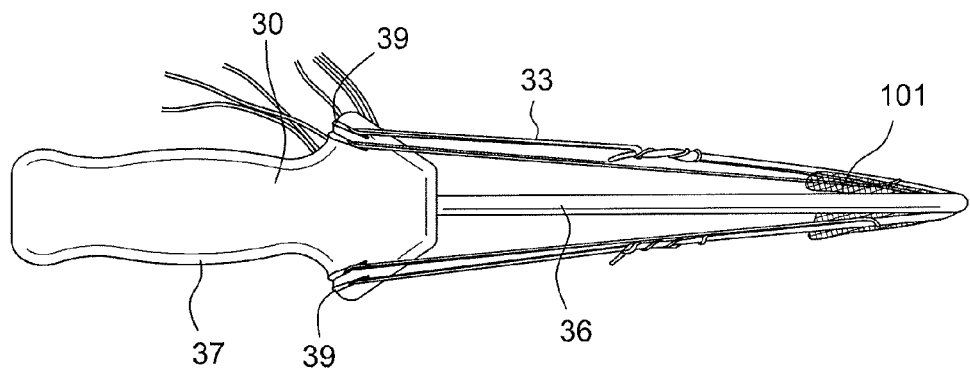
Figure 6:
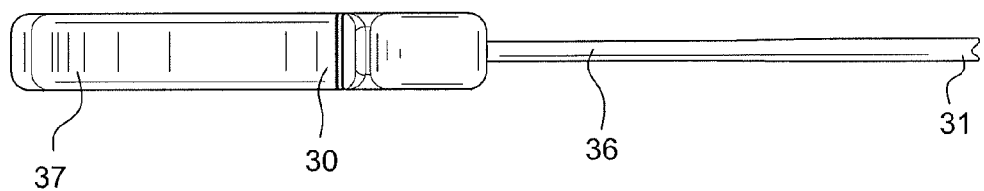

FIGS. 5-11 illustrate various views of driver 30 having a specific tip configuration for inserting mesh 101, 102, 103. In an exemplary embodiment, driver 30 may be provided as a package or assembly with the graft mesh already loaded onto the driver (as shown in FIG. 5, for example). In additional embodiments, driver 30 may be provided as a package or assembly with the graft mesh already loaded, and also with a dilator packed within the package.

The driver 30 is provided with a shaft 36 and handle 37 that are cannulated throughout their length. Tip 31 of the shaft 36 of driver 30 may have a saddle configuration (FIG. 7) to cradle the graft securely during insertion. Details of saddle 34 of tip 31 are shown in FIGS. 7 and 8. A suture 32 (FIG. 8) is placed in the cannulation of the shaft 36 to hold the mesh and/or the graft in place. The handle 37 of the driver 30 is preferably provided with at least one cleat or similar securing device 39 (preferably with two cleats 39) to allow sutures from the mesh and the graft to be securely attached to the handle (for example, by wrapping the sutures around the cleats). The driver may be provided in various sizes corresponding to respective sizes of the mesh and/or grafts and/or sockets.

FIG. 9 illustrates the mesh 101 of the present invention with two sutures 33 threaded through the mesh to secure the graft. FIGS. 10 and 11 illustrate the loading of mesh 101 through suture loop 32 of the driver 30. Additional sutures in mesh are now ready to accept the graft.

FIGS. 12-20 illustrate an exemplary femoral fixation technique, for fixation of a graft or ligament 50 within a femoral socket or tunnel formed within femur 80, and employing the mesh and driver of the present invention. FIGS. 12-14 illustrate graft 50 placed over the tip 31 of the driver 30 and over the mesh 101 (folded over the mesh 101). The ends of the graft 50 are placed through the suture loop 32. The sutures are tensioned securing the graft 50 to the mesh 101.

Figure 15:
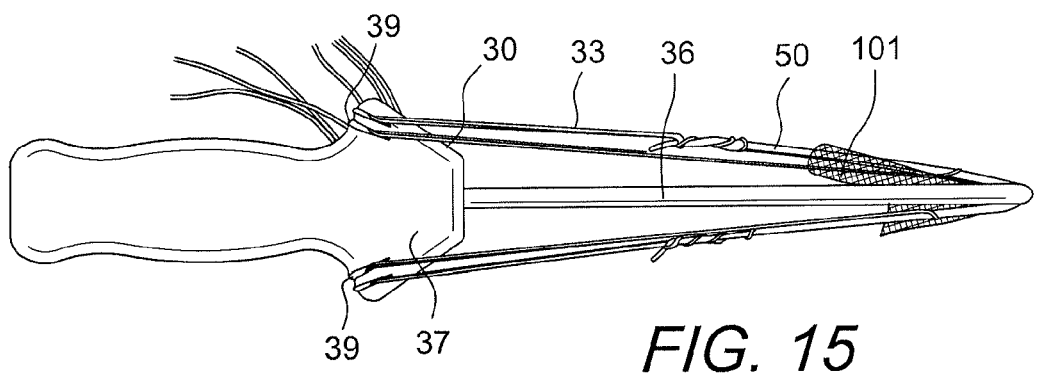
Figure 16:
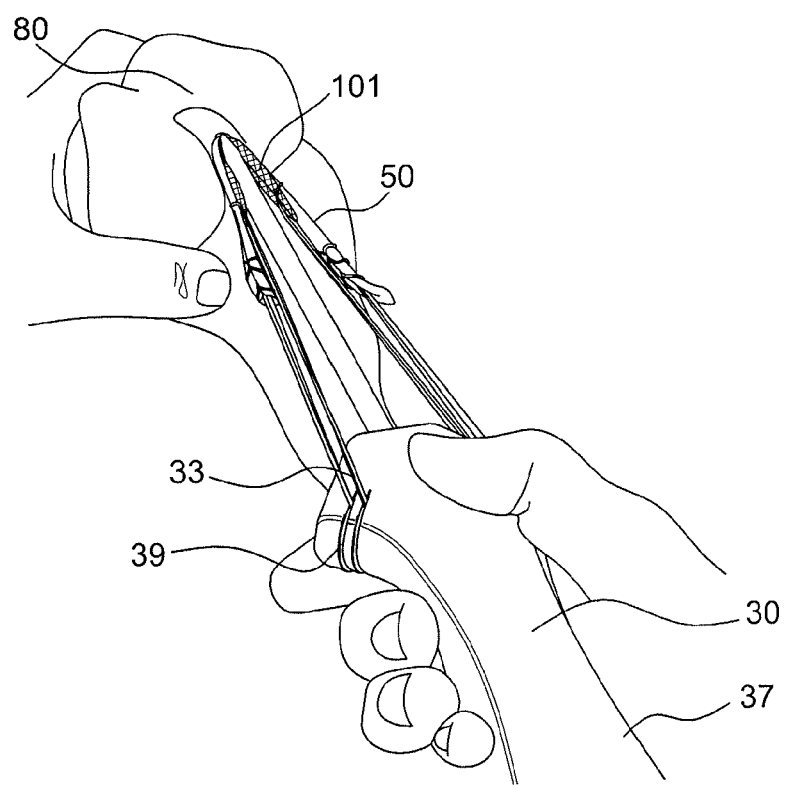
Figures 19A, 19B:
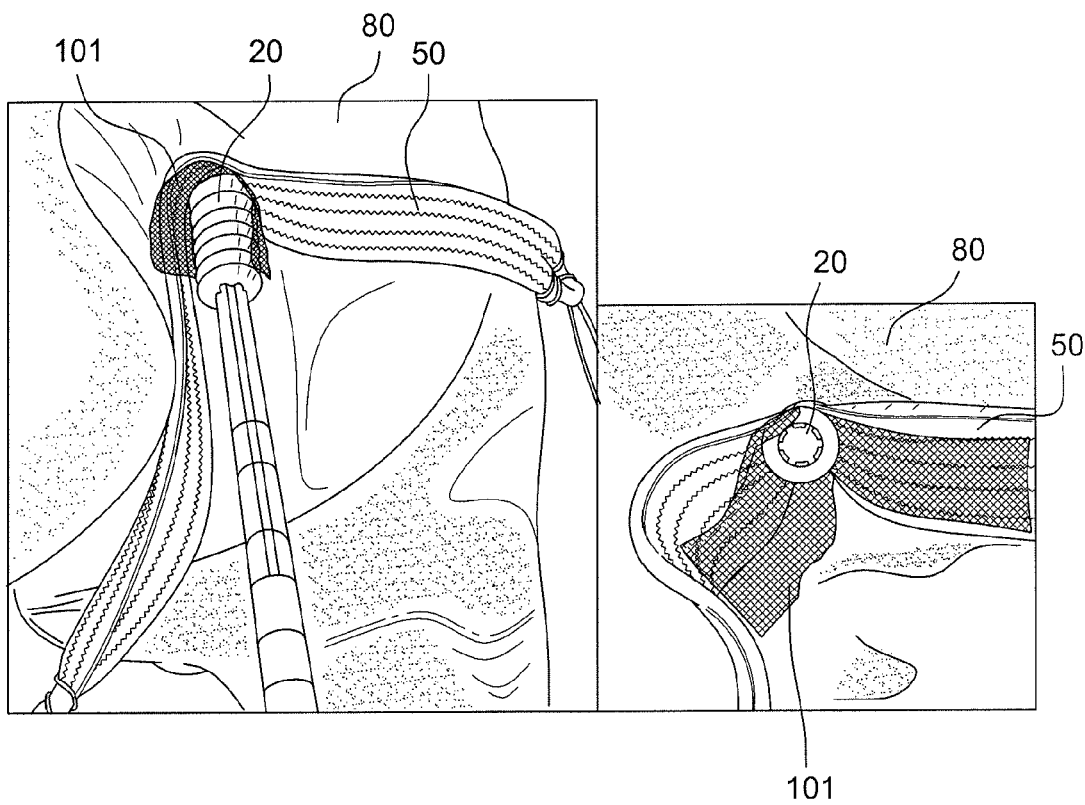
Figure 20:
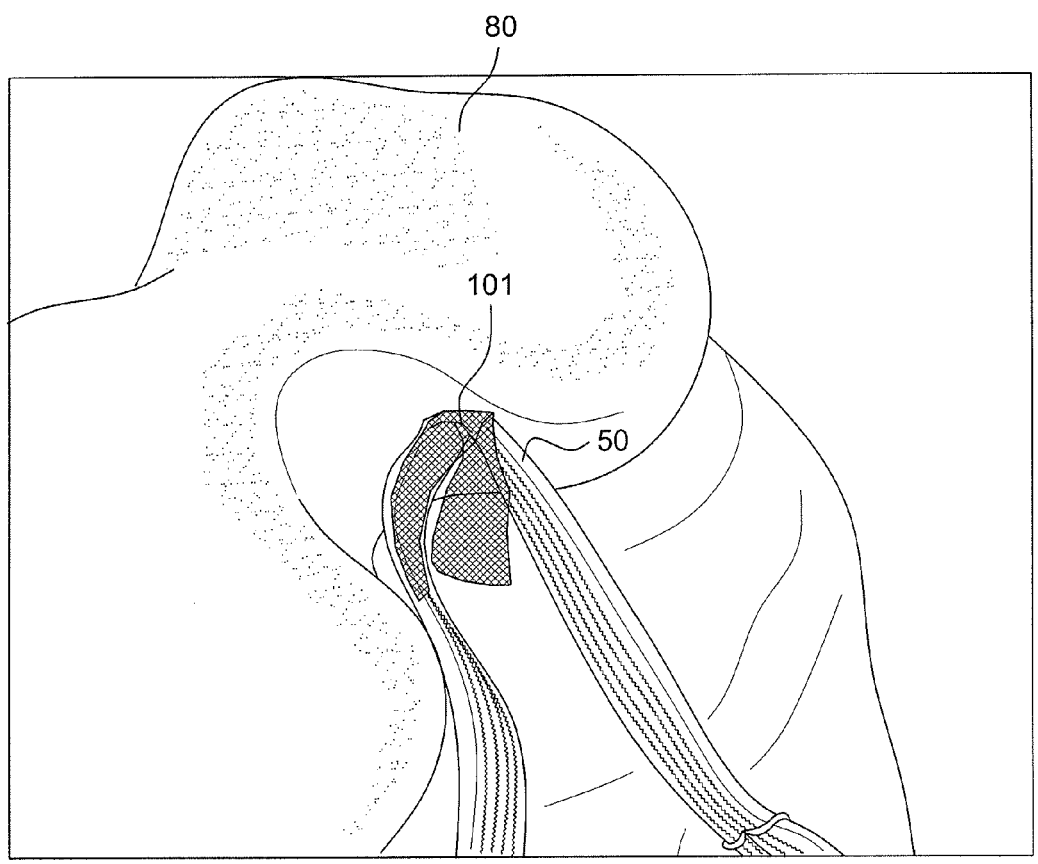

FIG. 15 illustrates sutures 33 from the mesh 101 and the graft 50 being wrapped around handle cleats 39. The device is ready for insertion. The graft 50 is placed into the socket of femur 80 using the driver 30 (FIG. 16). Suture (which secures mesh to driver during insertion) is removed from the driver cannulation, as shown in FIG. 17(a), and replaced by a guide wire 88 (for example, a nitinol guide wire 88), as shown in FIG. 17(b). The sutures from the graft and mesh are now removed (FIGS. 18(a) and (b)). The driver is removed and a fixation device 20 (for example, a screw 20 provided on a screwdriver) is placed over the nitinol wire 88 and inserted between the graft strands (FIGS. 19(a) and (b)). FIG. 20 illustrates the final femoral construct with the graft bundles separated.

Figure 21:
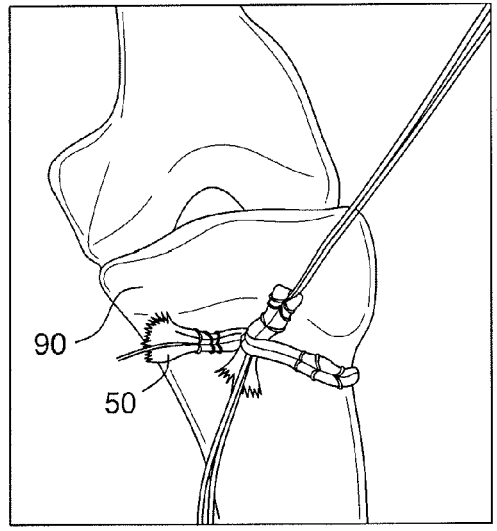
FIGS. 21-29 illustrate subsequent steps of a tibial fixation technique employing the driver/mesh assembly of FIG. 11, and according to an embodiment of the present invention.
Figure 22:
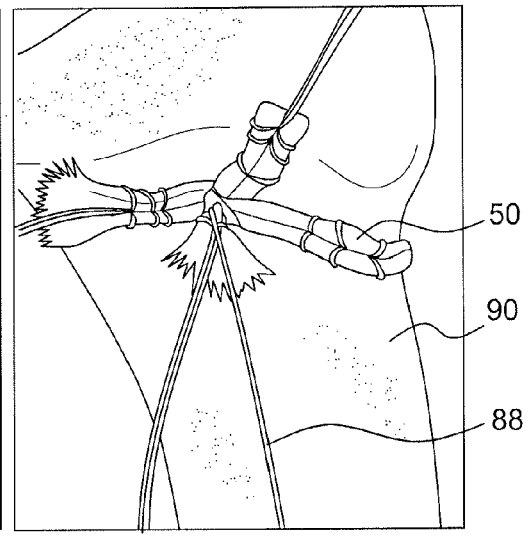
Figure 23:
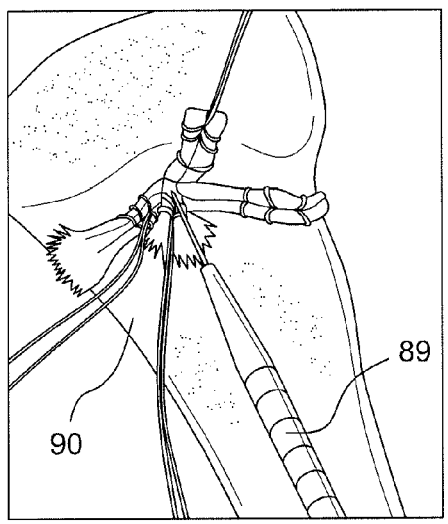
Figure 24:
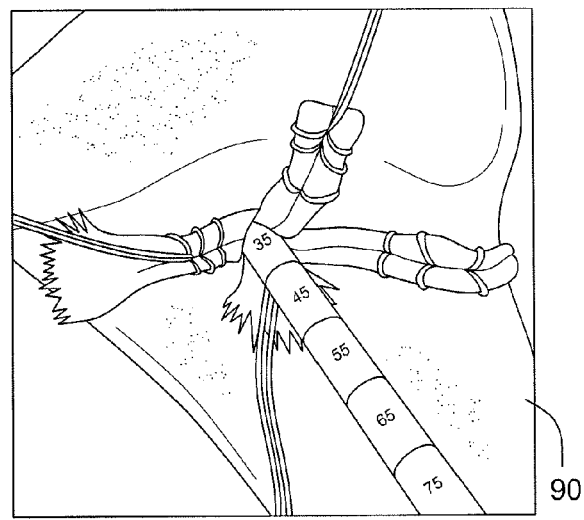
Figure 25:
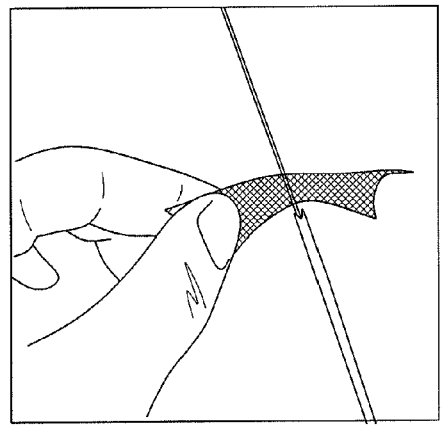
Figure 26:
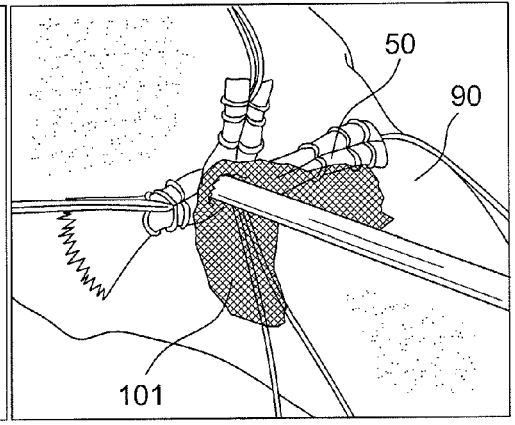
Figure 27:
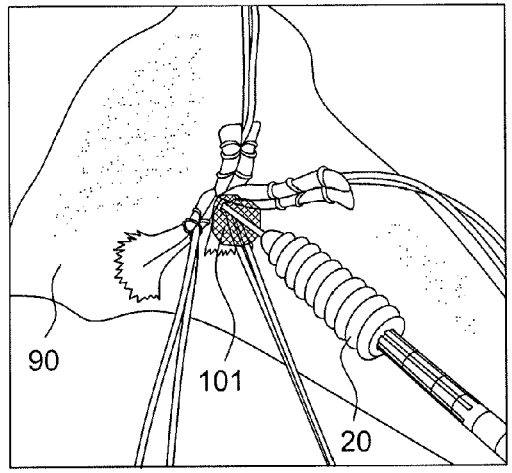
Figure 28:
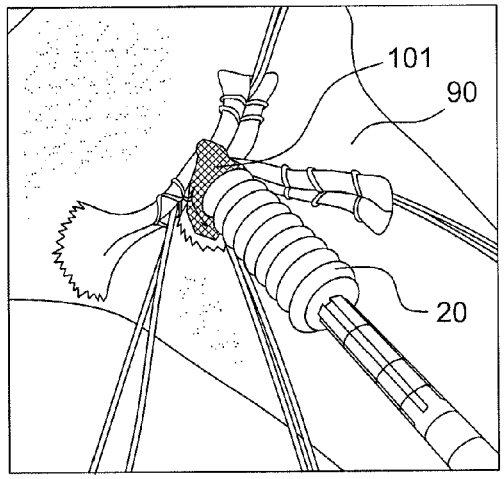
Figure 29:
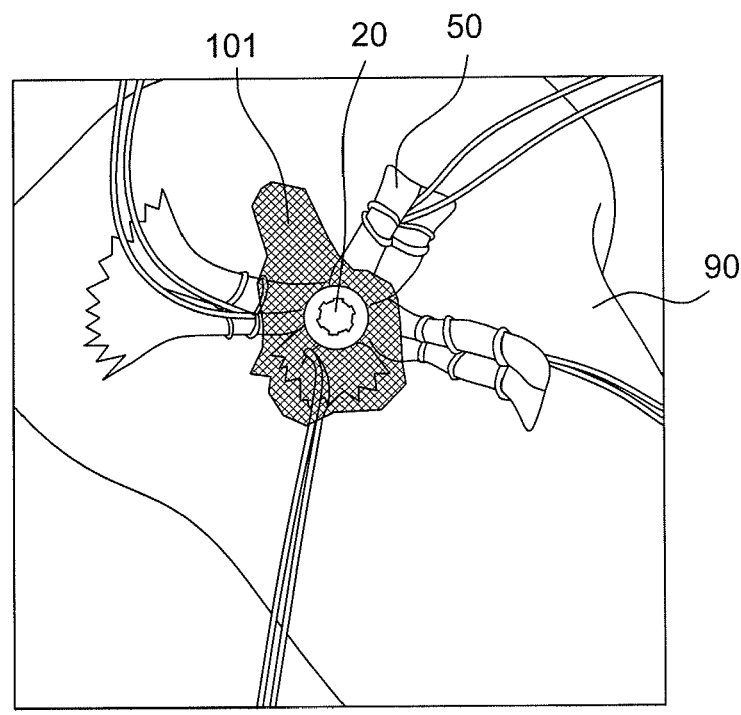

FIGS. 21-29 illustrate an exemplary tibial fixation technique, for fixation of a graft or ligament 50 within a tibial socket or tunnel formed within tibia 90, and employing the mesh and driver of the present invention. FIGS. 21 and 22 show the limbs of graft 50 spread and tensioned and a guide wire 88 placed in the center. A dilator 89 is placed over the wire 88 and impacted into tibia a distance equal to the length of the fixation device, i.e., a screw (FIGS. 23 and 24). The graft mesh 101 is inserted over the wire 88 and the inserter is used to place the graft mesh 101 into the tibial tunnel (FIGS. 25 and 26). A fixation device 20 (for example, a screw 20) is inserted over the wire 88 and into the tunnel against the mesh 101 pushing graft 50 against tunnel walls (FIGS. 27 and 28). FIG. 29 shows the final tibial construct.

FIGS. 31-35 illustrate a driver/mesh assembly 200 of the present invention with driver 130 designed to be employed with a mesh of the present invention (for example, with the mesh 104 of FIG. 30). FIGS. 36-42 illustrate exemplary steps of a femoral fixation technique employing the driver/mesh assembly 200 of FIG. 31.

An exemplary femoral fixation technique, for fixation of a graft or ligament 50 within a femoral socket or tunnel 81 formed within femur 80, and employing the mesh and driver 200 of the present invention, is illustrated in FIGS. 33-42.

Figure 33:
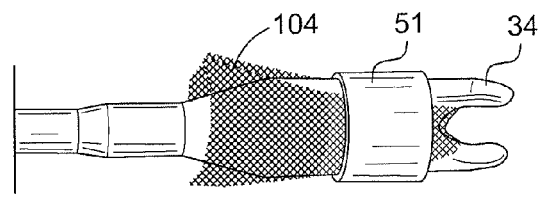
Figure 34:
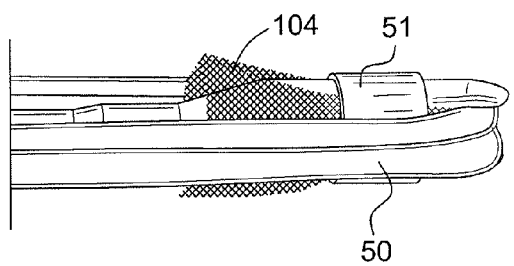
Figure 35:
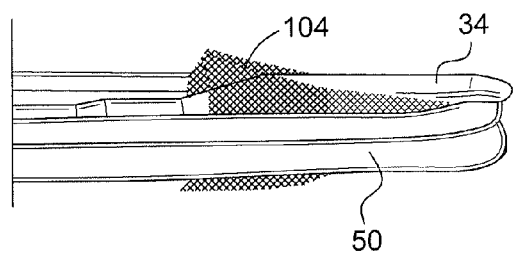
Figure 37:
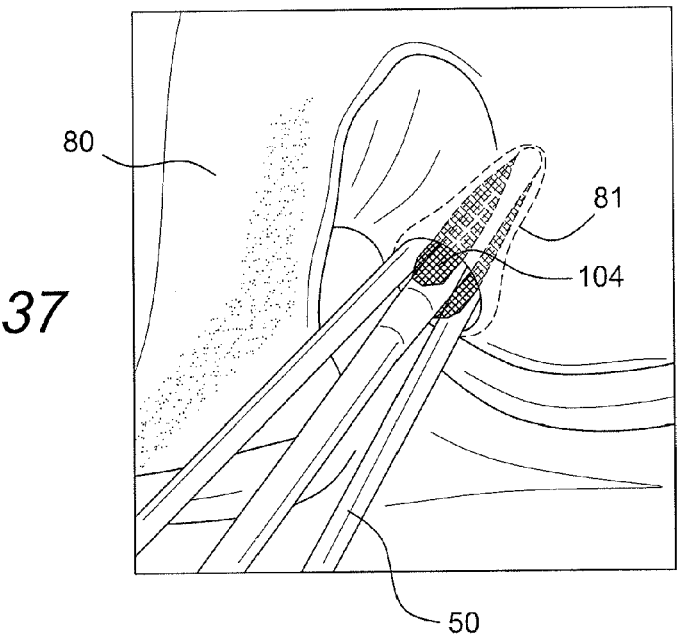
Figure 36:
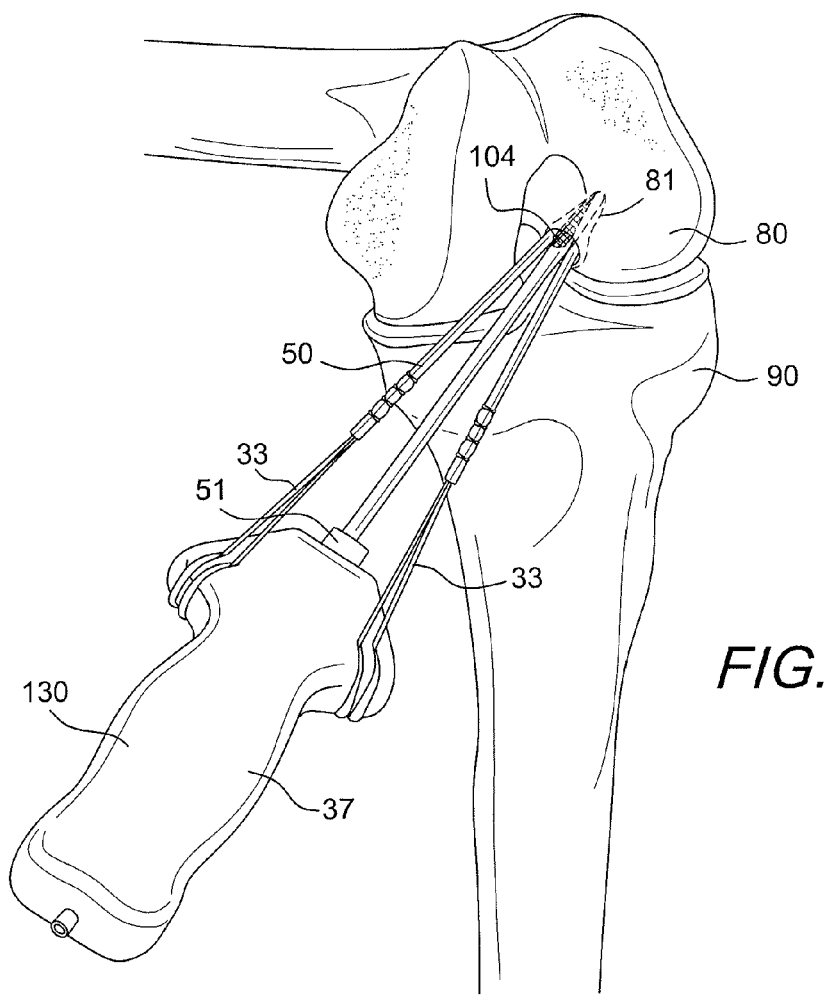

FIGS. 34-35 show mesh and driver 200 of the present invention with graft 50 placed over saddle 34 of tip 31 of driver 130, and also provided with an additional fixation device 51 (for example, in the form of a clear ring 51, as shown in FIGS. 33 and 34). Fixation device 51 is easily fitted around the mesh 104 and provides additional support for graft 50 which folds over (loops around) the mesh 104 and the saddle 34 of the shaft of the driver 130. Ring 51 is moved out of way and up shaft, towards the handle, before insertion.

Figure 41:
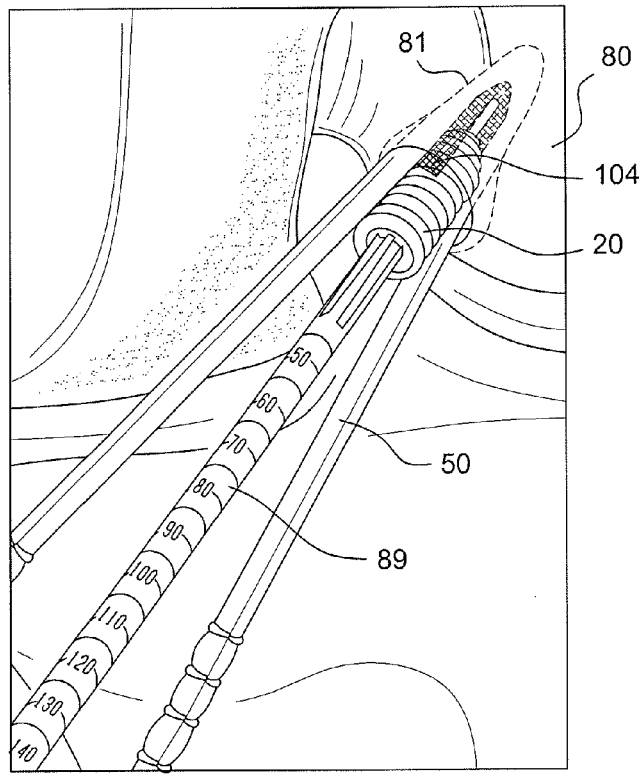
Figure 42:
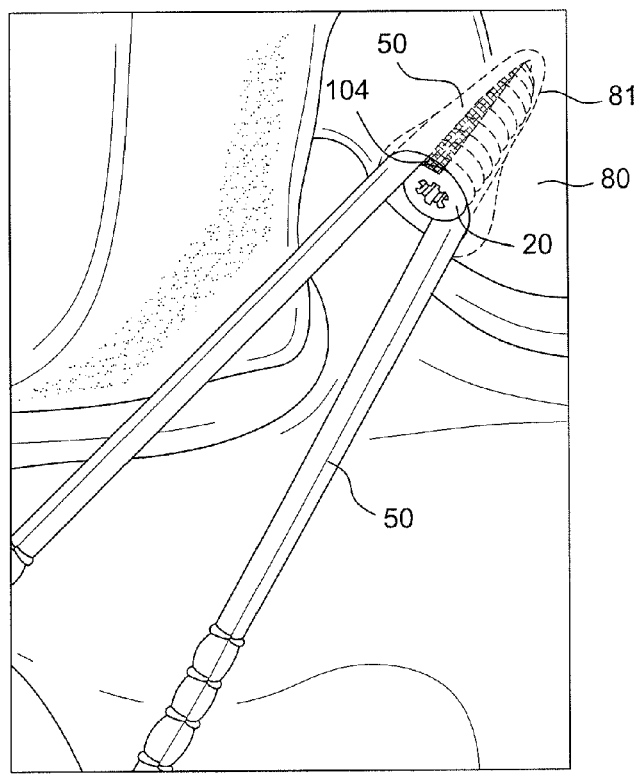

The limbs of graft 50 are spread and tensioned by employing sutures 33 (attached to the graft 50 and the mesh 104), which may be wrapped around cleats 39 on the handle 37 of the driver 130, as shown in FIG. 38. A guide wire 88 is placed in the center (and through the cannulation in the handle 37 and the shaft 36 of the driver 130), as shown in FIGS. 39 and 40. The inserter is removed and a dilator 89 is placed over the guide wire 88 and impacted into the tunnel a set length equal to the length of the fixation device 20 (for example, interference screw 20, as shown in FIG. 41). A fixation device 20 (for example, an interference screw 20) is inserted over the wire and into the femoral tunnel 81 between the mesh 104 which protects graft 50 (FIGS. 41 and 42). FIG. 42 shows the final femoral construct.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed as new and desired to be protected by Letters Patent of the United States is:

1. A method of graft fixation, the method comprising the steps of:
    forming a graft/mesh assembly comprising a graft and a mesh in contact with each other by folding the graft and the mesh over an end of a fixation device, such that the graft/mesh assembly extends from a first axial side of the fixation device, over the end of the fixation device, to a second axial side of the fixation device;
    introducing the graft/mesh assembly within a bone tunnel or socket;
    inserting the fixation device within the bone tunnel or socket to secure the graft/mesh assembly within the bone tunnel or socket, and to prevent rotation of the graft within the bone tunnel or socket.

2. The method of claim 1, wherein the graft is folded over the mesh.

3. The method of claim 1, wherein the mesh is folded over the graft.

4. The method of claim 1, wherein the step of introducing the graft/mesh assembly within the bone tunnel or socket further comprises the steps of: providing a flat, flexible mesh; sizing the mesh by medical personnel based on dimensions of the graft and on diameter of the bone tunnel or socket; folding the graft over the mesh; subsequently, folding the graft and the mesh over a tip of a driver; and inserting the folded graft and mesh within the bone tunnel or socket.

5. The method of claim 1, wherein the mesh has a collapsible configuration, to allow insertion within the bone tunnel or socket.

* * * * *